US006818662B2

(12) United States Patent
Ito et al.

(10) Patent No.: US 6,818,662 B2
(45) Date of Patent: Nov. 16, 2004

(54) PHARMACEUTICAL COMPOSITION

(75) Inventors: Shusei Ito, Tokyo (JP); Akio Miwa, Tokyo (JP); Mari Nakano, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/217,551

(22) Filed: Aug. 14, 2002

(65) Prior Publication Data

US 2003/0225032 A1 Dec. 4, 2003

(30) Foreign Application Priority Data

May 28, 2002 (JP) ........................................ 2002-154624

(51) Int. Cl.[7] ...................... A61K 31/71; A61K 31/715
(52) U.S. Cl. ........................... 514/361; 514/19; 514/58; 514/788; 514/227.8; 514/251.2; 514/431; 424/488; 564/229; 564/161; 564/218; 536/103; 544/370
(58) Field of Search ........................... 514/361, 19, 58, 514/788, 227.8, 231.2, 431; 424/488; 564/229, 161, 218; 536/103; 544/370

(56) References Cited

U.S. PATENT DOCUMENTS

| 3,502,720 A | * | 3/1970 | Amdt et al. | ................. 260/564 |
| 4,237,168 A | * | 12/1980 | Reifschneider | ............. 424/326 |
| 5,134,127 A | * | 7/1992 | Stella et al. | ................... 514/58 |

FOREIGN PATENT DOCUMENTS

| JP | 9-2977 A | | 1/1997 |
| WO | WO 85/02767 | | 7/1985 |
| WO | WO 94/02518 A1 | | 2/1994 |
| WO | WO 01/32164 A1 | | 5/2001 |
| WO | WO 01/32164 | * | 5/2001 |
| WO | WO 02/088071 A1 | | 7/2002 |

* cited by examiner

Primary Examiner—Elli Peselev
Assistant Examiner—Devesh Khare
(74) Attorney, Agent, or Firm—Sughrue Mion, PLLC

(57) ABSTRACT

The present invention provides a pharmaceutical composition comprising N-(3-chloro-4-morpholin-4-yl)phenyl-N'-hydroxyimidoformamidine and sulfobutyl ether β-cyclodextrin or a salt thereof, wherein sulfobutyl ether β-cyclodextrin increases the solubility of N-(3-chloro-4-morpholin-4-yl)phenyl-N'-hydroxyimidoformamidine and improves the photostability.

3 Claims, No Drawings

PHARMACEUTICAL COMPOSITION

BACKGROUND OF THE INVENTION

The present invention relates to a pharmaceutical composition which can contain N-(3-chloro-4-morpholin-4-yl)phenyl-N'-hydroxyimidoformamidine dissolved at high concentration, is stable and has a consistent quality.

N-(3-Chloro-4-morpholin-4-yl)phenyl-N'-hydroxyimidoformamidine is a compound which is disclosed in WO01/32164, and is recognized to have a capability for selectively inhibiting 20-HETE-producing enzyme to control stroke.

As known methods for improving the solubility of slightly water-soluble drugs to obtain injectable solutions, etc., there are methods for forming them into salts, micelles, co-solvents and lipid emulsion preparations and methods of incorporating β-cyclodextrins.

With respect to the solubilization of the slightly water-soluble drugs by incorporating β-cyclodextrins, WO85/02767 discloses a solubilization of the slightly water-soluble drugs by hydroxypropyl β-cyclodextrin, and U.S. Pat. No. 5,134,127 discloses a solubilization of the slightly water-soluble drugs by sulfobutyl ether β-cyclodextrin.

However, no suitable method for solubilization can easily be obtained due to the differences in the kind or characteristics of drugs. Furthermore, even if it can be solubilized, various problems may raise in respect of stability over time and in respect of safety.

N-(3-Chloro-4-morpholin-4-yl)phenyl-N'-hydroxyimidoformamidine is preferably administered by an intravenous route, but it is very slightly soluble in water and unstable under light exposure in a solution state, therefore, some special measures have been necessary to make a pharmaceutical composition such as an injectable solution. In addition, for prevention or therapy of stroke, since the prolonged intravenous infusion should be also considered, it is necessary to take the safety to a living body into consideration on the occasion of the production of the pharmaceutical preparation.

An object of the present invention is to provide a pharmaceutical composition which can contain N-(3-chloro-4-morpholin-4-yl)phenyl-N'-hydroxyimidoformamidine dissolved at high concentration, and is stable to light exposure, and safe to a living body.

SUMMARY OF THE INVENTION

As a result of repeated studies in order to attain the above-mentioned objects, the present inventors have found that by adding sulfobutyl ether β-cyclodextrin or a salt thereof to N-(3-chloro-4-morpholin-4-yl)phenyl-N'-hydroxyimidoformamidine, a preparation can be obtained which can contain the drug dissolved at high concentration, is improved in the stability over light exposure and safe without causing injuries to a living body by administration. The present invention has been accomplished on the basis of this finding. That is, the present invention is directed to a pharmaceutical composition which comprises a pharmaceutically effective amount of N-(3-chloro-4-morpholin-4-yl)phenyl-N'-hydroxyimidoformamidine, and sulfobutyl ether β-cyclodextrin or a salt thereof. The pharmaceutical composition of the present invention can be mainly used as an injectable solution and its further stability over time can be guaranteed by forming it into a freeze-dried injectable preparation.

DETAILED DESCRIPTION OF THE INVENTION

The present invention can be disclosed in more detail as follows. Since N-(3-chloro-4-morpholin-4-yl)phenyl-N'-hydroxyimidoformamidine was unstable in an acidic solution, solubilization by forming it into an acidic salt thereof was not proper. Furthermore, the solubility of N-(3-chloro-4-morpholin-4-yl)phenyl-N'-hydroxyimidoformamidine in 5% Tween 80, 10% polyethylene glycol, soybean oil and olive oil, which were used for forming it into micelles, co-solvents and lipid emulsion preparations, was not more than 0.5 mg/mL at 25° C. and was insufficient for forming it into these micelles, co-solvents and lipid emulsion preparations. However, in the case of a 10% aqueous solution of sulfobutyl ether β-cyclodextrin sodium salt, the solubility of N-(3-chloro-4-morpholin-4-yl)phenyl-N'-hydroxyimidoformamidine in the aqueous solution of sulfobutyl ether β-cyclodextrin or a salt thereof is 3.57 mg/mL at 25° C., and in the case of a 20% aqueous solution, the drug solubility is extremely high at 7.67 mg/mL at 25° C. Based on this unpredictable finding in which in the case of the sulfobutyl ether β-cyclodextrin solution, the drug is stable over light exposure and thus, it is convenient for actual use without a special care such as shading, the present invention has been accomplished.

In the present invention, N-(3-chloro-4-morpholin-4-yl)phenyl-N'-hydroxyimidoformamidine can be synthesized, for example, according to the method described in WO01/32164, and the dose is different depending on the disorders and administration forms, but it is 0.1 to 3000 mg per day, and preferably 1 to 300 mg per day.

Sulfobutyl ether β-cyclodextrin or a salt thereof is available as a commercial product (for example, Captisol (trade name) manufactured by CyDex, Inc.) or can be synthesized by introducing sulfobutyl group(s) into OH group(s) of β-cyclodextrin according to the method described in U.S. Pat. No. 5,134,127. The number of sulfobutyl group(s) substituted at OH group(s) of β-cyclodextrin is referred to as "substitution degree". The average substitution degree is preferably about 5 to about 8, more preferably about 6 to about 7, most preferably about 7. A preferred salt of sulfobutyl ether β-cyclodextrin is sodium salt.

Sulfobutyl ether β-cyclodextrin or a salt thereof is contained in an amount of 10 to 300 parts by weight, preferably 50 to 150 parts by weight based on one part by weight of N-(3-chloro-4-morpholin-4-yl)phenyl-N'-hydroxyimidoformamidine.

In addition, if necessary, tonicity agents (e.g., glycerol or glucose), pH modulators, etc. can be contained.

The pharmaceutical composition of the present invention may be formulated into various pharmaceutical forms such as injectable solutions, freeze-dried injectable preparations, tablets, granules, powders, capsules, solutions for internal use or dry syrups. Especially, injectable solutions and freeze-dried injectable preparations are preferred. These injectable solutions and freeze-dried injectable preparations can be dosed by single administration or intravenous infusion.

The pharmaceutical composition of the present invention can be formulated by usual preparation methods, for example, an ordinary method for producing injectable preparations which comprises mixing N-(3-chloro-4-morpholin-4-yl)phenyl-N'-hydroxyimidoformamidine, sulfobutyl ether β-cyclodextrin or a salt thereof and water for injection with agitation and dissolving the mixture. Specifically, there is a method which comprises adding water for injection to the powders of N-(3-chloro-4-morpholin-4-yl)phenyl-N'-hydroxyimidoformamidine and sulfobutyl ether β-cyclodextrin or a salt thereof and dissolving the mixture, or a method which comprises dissolving sulfobutyl ether β-cyclodextrin or a salt thereof in water for injection previously, adding N-(3-chloro-4-morpholin-4-yl)phenyl-N'-hydroxyimidoformamidine to the resulting solution and dissolving the mixture.

Agitation is usually carried out by means of an ordinary agitator, however, for certain purposes such as shortening the dissolution time, it can be carried out using an emulsifier or a homogenizer using a shearing force or a grinding force may be employed.

Conventional high-pressure steam sterilization and filtration sterilization are considered as sterilization step for preparation of injectable solutions, but in the case of the pharmaceutical composition of the present invention, high-pressure steam sterilization tends to lower the content of the drug, so that filtration sterilization is preferred. Usually, filtration sterilization can be carried out using a filter with a pore size of about 0.2 μm. The material of the filter will not be especially limited, unless there is any problem such as adsorption.

For producing freeze-dried injectable preparations, an ordinary freeze-drier can be used. Furthermore, in order to prevent the decomposition of the drug, the headspaces of vials or ampoules are preferably substituted with nitrogen regardless of the solution state of the composition or freeze-dried state.

Embodiments

The present invention is illustrated in more detail by the following examples and test examples.

EXAMPLE 1

N-(3-Chloro-4-morpholin-4-yl)phenyl-N'-hydroxyimidoformamidine (1 g) and sulfobutyl ether β-cyclodextrin sodium salt (Captisol (trade name); average substitution degree is about 7) (110 g) were weighed and distilled water for injection (1 L) was added; after dispersing by an agitator, the mixture was dissolved using a homogenizer. Then, the solution was sterilized by filtration using a filter (pore size: 0.22 μm). The solution (10 mL) was filled into a 20 mL-amber vial. The headspace of each vial was replaced with nitrogen; and the vials were stopped and sealed to give an injectable solution containing 1 mg/mL of the drug.

EXAMPLE 2

N-(3-Chloro-4-morpholin-4-yl)phenyl-N'-hydroxyimidoformamidine (1 g) and sulfobutyl ether β-cyclodextrin sodium salt (Captisol (trade name); average substitution degree is about 7) (110 g) were weighed and distilled water for injection (1 L) was added; after dispersing by an agitator, the mixture was dissolved using a homogenizer. Then, the solution was sterilized by filtration using a filter (pore size:0.22 μm). The solution (10 mL) was filled into a 20 mL-amber vial and subjected to freeze-drying in which the shelf-temperature was set at −10° C. The headspace of each vial was replaced with nitrogen; and the vials were stopped and sealed to give a freeze-dried injectable preparation containing 10 mg of the drug per vial.

COMPARATIVE EXAMPLE 1

A saturated aqueous solution of N-(3-chloro-4-morpholin-4-yl)phenyl-N'-hydroxyimidoformamidine was obtained in the same manner as in Example 1 except that sulfobutyl ether β-cyclodextrin sodium salt was not used.

COMPARATIVE EXAMPLE 2

A freeze-dried injectable preparation of N-(3-Chloro-4-morpholin-4-yl)phenyl-N'-hydroxyimidoformamidine was obtained in the same manner as in Example 2 except that 100 g of hydroxypropyl β-cyclodextrin and 30 g of d-mannitol as a tonicity agent were used instead of 110 g of sulfobutyl ether β-cyclodextrin sodium salt.

TEST EXAMPLE 1

[Solubilization Test]

An excess amount of N-(3-chloro-4-morpholin-4-yl)phenyl-N'-hydroxyimidoformamidine was added to 10% and 20% aqueous solutions of sulfobutyl ether β-cyclodextrin sodium salt (Captisol (trade name); average substitution degree is about 7) and purified water as a control, respectively. After shaking on a water bath adjusted at 25° C. for one day, the solubility of the drug was measured.

As a result, the solubility of N-(3-chloro-4-morpholin-4-yl)phenyl-N'-hydroxyimidoformamidine in purified water as a control was 0.08 mg/mL and it was found to increase upon addition of sulfobutyl ether β-cyclodextrin sodium salt to the solutions as shown in Table 1. Accordingly, sulfobutyl ether β-cyclodextrin is shown to be useful for dissolution of N-(3-chloro-4-morpholin-4-yl)phenyl-N'-hydroxyimidoformamidine.

TABLE 1

| Concentration of sulfobutyl ether β-cyclodextrin | Solubility |
| --- | --- |
| 10% | 3.57 mg/mL |
| 20% | 7.67 mg/mL |

TEST EXAMPLE 2

[Photostability Test]

The solution of Example 1 and the solution of the Comparative Example 1 were each put into a colorless and transparent capped glass tube, and preserved under the fluorescence light condition of 3000 lux, and the remaining rates of N-(3-chloro-4-morpholin-4-yl)phenyl-N'-hydroxyimidoformamidine were measured. As a result, N-(3-chloro-4-morpholin-4-yl)phenyl-N'-hydroxyimidoformamidine in the solution of Example 1 was much more stable than that in the solution of the Comparative Example 1 as shown in Table 2. Accordingly, sulfobutyl ether β-cyclodextrin was shown to be very useful for the stability of N-(3-chloro-4-morpholin-4-yl)phenyl-N'-hydroxyimidoformamidine.

TABLE 2

|  | Example 1 | Comparative Example 1 |
| --- | --- | --- |
| preservation period (hrs) | 48 | 24 |
| remaining rate (%) | 97.8 | 38.7 |

TEST EXAMPLE 3

[Stability Test in Freeze-dried Injectable Preparation]

After preservation of the freeze-dried injectable preparation of Example 2 and the freeze-dried injectable preparation of Comparative Example 2 at 60° C. for 7 days, the remaining rates of the drug thereof were measured. As a result, N-(3-chloro-4-morpholin-4-yl)phenyl-N'-hydroxyimidoformamidine in the freeze-dried injectable preparation of Example 2 was more stable than that in the freeze-dried injectable preparation of Comparative Example 2 as shown in Table 3. Accordingly, sulfobutyl ether β-cyclodextrin was shown to be very useful for the stability of N-(3-chloro-4-morpholin-4-yl)phenyl-N'-hydroxyimidoformamidine.

TABLE 3

|  | Example 2 | Comparative Example 2 |
|---|---|---|
| preservation period (days) | 7 | 7 |
| remaining rate (%) | 99.4 | 97.8 |

As a conclusion, the freeze-dried injectable preparation of the pharmaceutical composition of the present invention was proved to have an excellent stability and good convenience on the occasion of actual preservation and use.

What is claimed is:

1. A pharmaceutical composition which comprises N-(3-chloro-4-morpholin-4-yl)phenyl-N'-hydroxyimidoformamidine and sulfobutyl ether β-cyclodextrin or a salt thereof and a pharmaceutically acceptable carrier.

2. The pharmaceutical composition according to claim 1 which is an injectable solution.

3. The pharmaceutical composition according to claim 1 which is a freeze-dried injectable preparation.

* * * * *